Dec. 13, 1960 O. O. DUNHAM Plant Pat. 2,006
CHRYSANTHEMUM PLANT
Filed July 27, 1959
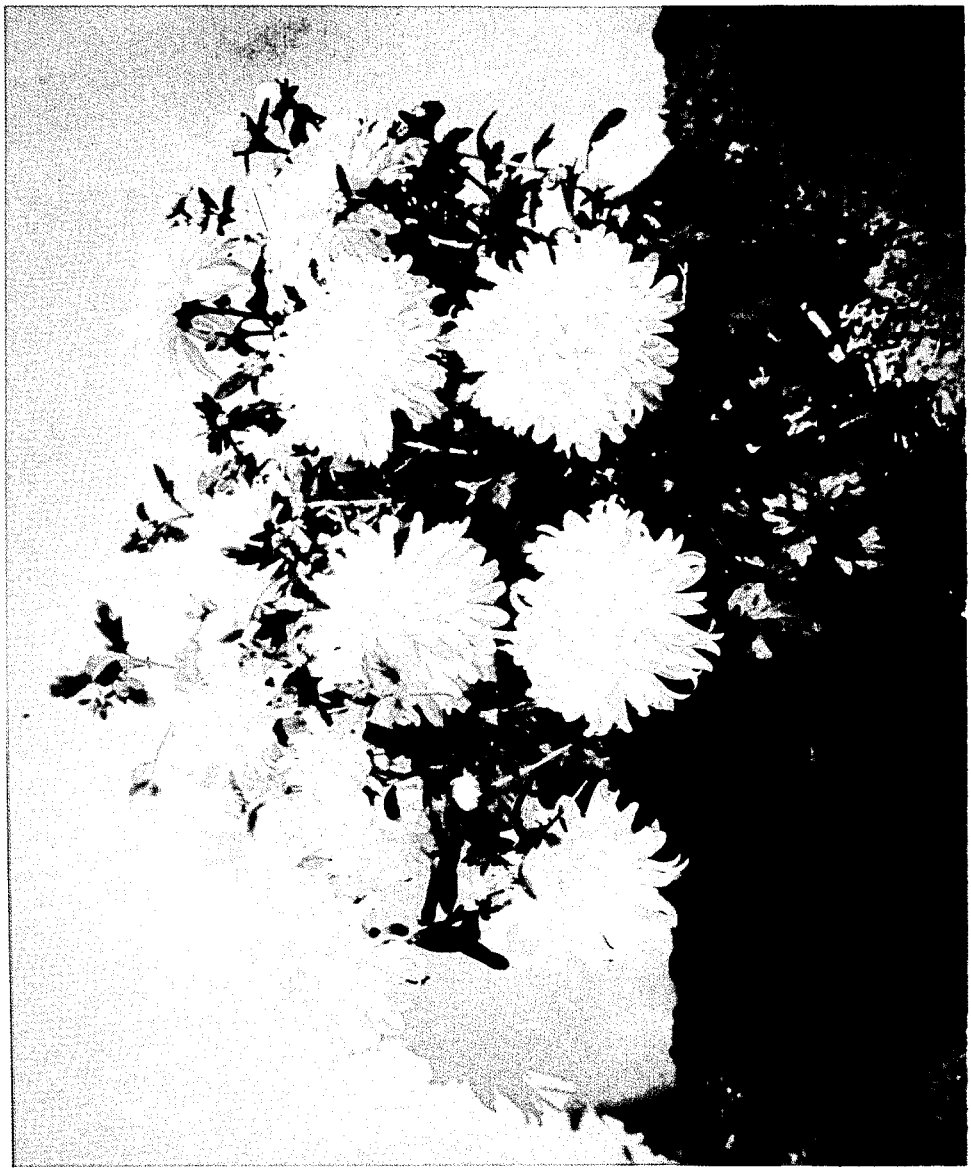
Inventor
O. O. Dunham
by Robb & Robb
attorneys United States Patent Office Plant Pat. 2,006
Patented Dec. 13, 1960

2,006

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,949

1 Claim. (Cl. 47—60)

My present invention comprises a new and distinct variety of chrysanthemum plant, the result of crossing the unpatented variety of my own origination known as "Coronet" and the unnamed variety of my own origination which I designate as "No. 5350."

The object of my invention has been to produce an improved variety of chrysanthemum having desirable characteristics of the so-called American garden chrysanthemum and the so-called English early chrysanthemum, the blossoms of this particular variety varying from brilliant yellow to vivid yellow (Nickerson Color Fan of Munsell Color Company).

The development of the present new variety is essentially the result of hybridizing in a program involving selection of certain of the most outstanding American garden chrysanthemums which are well known and the English early chrysanthemums previously referred to, in a program which has been characterized by careful selection and cross-breeding with the view of producing new varieties of chrysanthemums having in many respects the important and desirable characteristics of both parents and colors which make the blooms of such plants outstanding and readily identifiable from prior varieties.

The result of the specific hybridization previously mentioned has been to produce this particular new and distinct variety of chrysanthemum plant which in general is characterized by the brilliant yellow color of its blooms varying to vivid yellow, the very double arrangement of its petals, the more dwarf, more compact and more vigorous habit of growth, and particularly its earlier and longer blooming period taken in conjunction with the more continuous, profuse, flowering with better flower form and color.

The blooms of this new variety are of medium size, borne in clusters and somewhat irregular. As grown in the vicinity of Niles, Michigan, the blooms appear on long, strong stems with very double petallage and innumerable petals.

While my new variety somewhat resembles the pollen parent "Coronet," the color and habit are substantially better than said variety.

The earliness, flower type and continuous blooming are contributed to the variety by the seed parent No. 5350. The combination of these two makes the instant variety earlier flowering, more continuous flowering with better habits and flower color.

It may be noted that while the pollen parent "Coronet" is of yellow ball type as to its flower, the seed parent No. 5350 is of an incurved pink type.

When the flowers are grown in the region of Niles, Michigan, a late September or early October flowering date is usual and continuous flowering is characteristic in contrast to the usual all at one time flowering of the American garden chrysanthemum which may extend over a period of a week or ten days. The variety herein will produce a continuous uninterrupted show of color from early in September until a killing frost.

My new variety has been asexually reproduced by cuttings, in the vicinity of Niles, Michigan.

My new variety has been found to retain its distinctive characteristics through successive asexual reproduction.

The accompanying drawing forming a part hereof shows a typical plant of my variety of chrysanthemum.

The following is a detailed description of my new variety of chrysanthemum plant, the color references being to the Nickerson Color Fan published by Munsell Color Company:

Parentage: Seedling.
- *Seed parent.*—No. 5350 (unpatented).
- *Pollen parent.*—"Coronet" (unpatented).

Classification: Botanic—*Chrysanthemum indicum.*

*Flower*

Blooming habit: Blooming early, profusely and continuously from early September until a killing frost.

Bud:
- *Size.*—Large.
- *Form.*—Short with flat top. Not affected by wet or hot weather. Sepals of no consequence.
- *Color.*—When petals begin to unfurl—between Munsell Hue 5Y 9/9 Brilliant Yellow and 5Y 8/12 Vivid Yellow. When half blown: inside of petals—Munsell Hue 5Y 8/12 Vivid Yellow; reverse of petals—Munsel Hue 7.5Y 9/8 Brilliant Greenish Yellow.
- *Peduncle.*—Very long.
- *Aspect.*—Rough.
- *Color.*—Medium green.
- *Strength.*—Stiff; erect.
- *Opening.*—Bud opens well; somewhat affected by adverse conditions.

Bloom:
- *Size.*—Medium.
- *Average size when fully expanded.*—4½ inches (disbudded).
- *Borne.*—In clusters; irregular.
- *Stems.*—Long; strong.
- *Form.*—When first opened—flat. Permanence—retains its form to the end.
- *Petalage.*—Very double. Number of petals under normal conditions—innumerable.
- *Color.*—Center of flower—5Y 9/9 Munsell Hue 5Y. Outer petals—5Y 9/9 Munsell Hue 5Y. Base of petals—5Y 9/9 Munsell Hue 5Y. Inside of petals—5Y 9/9 Munsell Hue 5Y. Reverse of petals—lighter than 5Y 9/9 Munsell Hue 5Y. General tonality from a distance—5Y 9/9 Munsell Hue 5Y.
- *Discoloration.*—General tonality at end of: First week—retains the same color. Second week—retains much the same color. Third week—retains much the same color.

Petals:
- *Texture.*—Thin. Affected by bleaching in hot weather. Affected by fungus infection in wet weather.
- *Appearance.*—Inside—velvety; outside—satiny.
- *Form.*—Pointed.
- *Arrangement.*—Imbricated
- *Persistance.*—Hang on and dry.
- *Lastingness.*—On the plant—very long. As cut flower—long.

Genital organs:
- *Stamens, anthers.*—Small; few. Color—yellow. Arrangement—regular around styles.
- *Stamens, filaments.*—Short. Color—white.
- *Styles.*—Columnar. Length—short.

*Stigmas.*—White.
*Ovaries.*—All enclosed in calyx.
Fruit: Variety is fertile with own pollen.
*Form.*—Oblong shaped.
*Aspect.*—Rough.
*Color at maturity.*—Brownish grey.

*Plant*

Form: Bush.
Growth: Vigorous; dwarf; branching; compact.
Foliage:
*Size.*—Large.
*Quantity.*—Abundant.
*Color.*—New foliage: upper side—normal green; under side—light green. Old foliage: upper side—dark green; under side—dark green.
*Shape.*—Three lobed.

*Texture.*—Upper side—velvety, flat. Under side—velvety. Ribs and veins—ordinary.
*Edge.*—Smooth.
*Leaf stem.*—Green in color. Under side—smooth.
*Stipules.*—Short.
*Disease resistance.*—Susceptible to mildew under certain conditions.

I claim:

A new and distinct variety of chrysanthemum plant substantially as herein disclosed, characterized as to novelty by the brilliant yellow color of its blooms, the very double arrangement of its petals, more dwarf, more compact and vigorous habit of growth, earlier and longer blooming period, and more continuous, profuse, flowering with better flower form and color.

No references cited.